United States Patent
Revivo

(10) Patent No.: US 9,351,921 B1
(45) Date of Patent: May 31, 2016

(54) MICRODERMABRASION CREAM

(71) Applicant: Rena Revivo, Sun Valley, CA (US)

(72) Inventor: Rena Revivo, Sun Valley, CA (US)

(73) Assignee: Spa De Soleil, Inc., Sun Valley, CA (US)

( * ) Notice: Subject to any disclaimer, the term of this patent is extended or adjusted under 35 U.S.C. 154(b) by 448 days.

(21) Appl. No.: 14/023,444

(22) Filed: Sep. 10, 2013

(51) Int. Cl.
*A61K 8/00* (2006.01)
*A61K 8/97* (2006.01)
*A61K 8/891* (2006.01)
*A61Q 19/08* (2006.01)

(52) U.S. Cl.
CPC . *A61K 8/97* (2013.01); *A61K 8/891* (2013.01); *A61Q 19/08* (2013.01)

(58) Field of Classification Search
CPC ......... A61Q 19/08; A61K 8/97; A61K 8/891; A01B 12/006
See application file for complete search history.

(56) References Cited

U.S. PATENT DOCUMENTS

| | | | |
|---|---|---|---|
| 5,556,887 A | 9/1996 | Lerner | |
| 5,653,970 A | 8/1997 | Vermeer | |
| 5,738,887 A * | 4/1998 | Wu | A23F 3/10 426/51 |
| 6,652,888 B2 | 11/2003 | Rhoades | |
| 6,696,067 B2 | 2/2004 | Brandt | |
| 8,241,618 B2 | 8/2012 | Brandt | |
| 2001/0023351 A1 | 9/2001 | Eilers | |
| 2007/0169285 A1* | 7/2007 | Narasimhan | A61K 8/31 8/405 |
| 2009/0094762 A1* | 4/2009 | Dawis | A61K 8/365 8/435 |
| 2010/0136168 A1* | 6/2010 | McHaney | A23L 1/2128 426/52 |
| 2011/0300081 A1* | 12/2011 | Seneci | A61K 9/0007 424/43 |
| 2014/0086858 A1* | 3/2014 | Doyle | A61K 8/361 424/60 |
| 2014/0212453 A1* | 7/2014 | Chang | A23L 1/0067 424/195.18 |
| 2014/0325778 A1* | 11/2014 | Chang | A46B 9/04 15/167.1 |
| 2015/0056255 A1* | 2/2015 | Ragot | A23L 2/395 424/401 |
| 2015/0064124 A1* | 3/2015 | Yontz | A61K 8/25 424/59 |

FOREIGN PATENT DOCUMENTS

EP    EP 1364639    11/2003

\* cited by examiner

*Primary Examiner* — Patricia A Leith
(74) *Attorney, Agent, or Firm* — Thomas I. Rozsa

(57) ABSTRACT

A microdermabrasion cream which eliminates the use of microcrystals which can potentially scar skins during a microdermabrasion process and is a cream which consists of the following combination of ingredients which can be safely utilized for microdermabrasion of facial skin. The present invention cream contains the following ingredients: deionized Water, Titanium Dioxide, Carbomer, Glycerin, Disodium EDTA, Caprylic/Capric Triglycerides, Polysorbate 20, *Citrus Limon* (Lemon) Peel Oil, Sodium Hydroxide, Menthol; Cyclomethicone, Dimethicone, *Carica Papaya* (Papaya Fruit), *Ananas Sativus* (Pineapple Fruit), *Cucumis Sativus* (Cucumber) Extract, Glycereth-7, *Bambusa Arundinacea* Stem Powder, Methylchloroisothiazolinone and Methylisothiazolinone.

3 Claims, No Drawings

MICRODERMABRASION CREAM

BACKGROUND OF THE INVENTION

1. Field of the Invention

The present invention relates to the field of cosmetic dermabrasion creams which are used with exfoliating machines such as rotating brushes to gently peal away the top layer of facial skin to provide a more youthful appearance.

2. Description of the Prior Art

The following seven patents and published patent applications are the closest prior art to the present invention:

1. U.S. Pat. No. 5,556,887 issued to Sheldon Lerner on Sep. 17, 1996 for "Improved a Palmitate Composition for Topical Application Which Achieves to the Entire Dermal Membrane" (hereafter the "Lerner Patent");
2. U.S. Pat. No. 5,653,970 issued to Robert Vermeer on Aug. 5, 1997 for "Personal Product Compositions Comprising Heteroatom Containing Aldyl Aldonamide Compounds" (hereafter the "Vermeer Patent");
3. United States Published Patent Application No. 2001/0023351 to George J. Eilers et al. on Sep. 20, 2001 for "Skin Abrasion System And Method" (hereafter the "Eilers Published Patent Application");
4. U.S. Pat. No. 6,652,888 issued to Dean L. Rhoades on Nov. 25, 2003 for "Method for Skin Rejuvenation With Buffing Cream" (hereafter the "Rhoades Patent");
5. U.S. Pat. No. 6,696,067 issued to Loralei Marie Brandt et al. on Feb. 24, 2004 for "Cosmetic Compositions Containing Dispersion Polymers" (hereafter the "'067 Brandt Patent");
6. U.S. Pat. No. 8,241,618 issued to Loralei Brandt et al. on Aug. 14, 2012 for "Process for Producing a Hydrophobically Modified Polymer for Use with Personal Care Compositions" (hereafter the "'618 Brandt Patent");
7. European Patent NO. EP 1,364,639 (hereafter the "European Patent").

The Lerner Patent Discloses:

"A stable, non-oily, Vitamin A Palmitate composition having a high water ratio for dermatogical application to human skin. Non-irritating thickeners, preservatives and carriers synergize to achieve optimal bioavailability. A method of application of the composition achieves repair and rejuvenation of the entire dermal membrane."

As set forth in the prior art, Vitamin A is well known for its nutritional and therapeutic qualities, especially for the epithelia. Fulton discussed the internal use of Vitamin A palmitate in U.S. Pat. No. 5,043,356.

The use of retinol palmitate is also disclosed in Column 2 Line 42. Vitamin A retonic acid is also disclosed in this patent.

The Vermeer Patent is an extremely long patent listing many ingredients. The patent discloses in Column 24, Lines 10 through 44 the following:

"Still another suitable class of nonionic surfactant useful in the present invention are the alkene oxide condensation products of polyhydroxyalkyl esters having about 8 to about 18 carbon atoms and about 1 to about 200 moles of ethylene or propylene oxide, preferably from about 3 to about 45 moles of ethylene or propylene oxide. Examples of polyhydroxyalkyl esters include those having about 2 to about 7 hydroxyl groups per alkyl chain such as ethylene glycol esters, propylene glycol esters, glycerol esters, polyglycerol esters, erythritol esters, xylitol esters, pentaerythritol esters, sorbitol/sorbitan esters, mannitol/mannitan esters, alkyl glucoside esters, glucose esters and sucrose esters. Specific examples include, but are not limited to PEG-12 glyceryl laurate, PEG-7 glyceryl cocoate, PEG-30 glyceryl cocoate, PEG-25 glyceryl oleate, PEG-200 glyceryl tallowate, PEG-200 glyceryl palmirate, PEG-4 glyceryl caprylate/caprate, PEG-8 glyceryl caprylate/caprate, PEG-55 propylene glycol oleate, PEG-55 propylene glycol oleate, sucrose stearate, sucrose distearate and the like.

Preferred polyhydroxypolyoxyalkylene alkyl esters useful in the present invention include the polyoxyalkylene sorbitan, and mannitan esters having about 8 to about 18 carbon atoms and about 3 to about 100 moles of ethylene oxide. Specific examples of polyoxyalkylene sorbitan and mannitan esters include the Tweens, such as polyoxyethylene (10) sorbitan monolaurate, polyoxyethylene (20) sorbitan monolaurate, polyoxyethylene (44) sorbitan monolaurate, polyoxyethylene (20) monopalmitate, polyoxyethylene (20) sorbitan monostearate, polyoxyethylene (10) sorbitan monococoate, polyoxyethylene (20) sorbitan monococoate, polyoxyethylene (30) marmitan dilaurate, polysorbate 20, polysorbate 21, polysorbate 60, polysorbate 61, polysorbate 65, polysorbate 80, polysorbate 85 and mixtures thereof."

The patent further discloses in Column 34 the following:

"Examples of polyols useful in the present invention include, but are not limited to propylene glycol (PG), dipropylene glycol, pentapropylene glycol, polypropylene glycol 2000 to 4000, polypropylene glycol 2000 to 4000 fatty acid esters, polyoxyethylene/polyoxypropylene glycols, polyoxypropylene/polyoxyethylene glycols, ethylene glycol, diethylene glycol, diethylene glycol mono/di-fatty acid esters, polyethylene glycol 200 to 6000 (PEG), polyethylene glycol 200 to 6000 mono/di-fatty acid esters, methoxy polyethylene glycol 350 to 5000, ethylene glycol mono/di-fatty acid esters, glycerol (glycerin), ethoxylated glycerol, propoxylated glycerol, glycerol mono/di/tri-fatty acid esters, polyglycerol, polyglycerol mono/di-fatty acid esters, erythritol, xylitol, sorbitol, sorbitan, ethoxylated sorbitol, hydroxypropyl sorbitol, mannitol, lactitol, hydrogenated starch hydrolyzates, 1,3-butylene glycol, 1,3-butylene glycol mono/di-esters, 1,2,6-hexane-triol, 2-ethyl-1,3-hexanediol, $C_{15}$-$C_{18}$ vincinal glycol, trimethanolethane, trimethyl-olpropane, ethoxylated trimethylolpropane, pentaerythritol, ethoxylated pentaerythritol, fructose, dextrin, glucose and the like. Preferred polyols are propylene glycol, propylene glycol stearate, propylene glycol dipelargonate, PEG-55 propylene glycol oleate, PEG-75, PEG-150, PEG-400, PPG-5 ceteth-20, ethylene glycol monostearate, ethylene glycol distearate, PEG-6 stearate, PEG-8 distearate, PEG-25 stearate, PEG-100 stearate, PEG-150 distearate, PEG-400 stearate, glycerin, diglycerin, decaglyceryl diisostearate, glyceryl laurate, glyceryl myristate, PEG-26 glycerate, caprylic/capric triglyceride, pentaerythrityl tetralaurate, sorbitan stearate, glycereth-7 and mixtures thereof."

The patent further discloses in Column 38 the following:

"The personal product compositions herein can contain a variety of less essential optional ingredients (auxillary agents) suitable for rendering such compositions more acceptable. Such ingredients are well known to those skilled in the art and include, but are not limited to viscosity control agents, dispersants, solubilizing/clarifying agents, stabilizers, sunscreens/UV absorbers, opacifiers/pearlescent agents, vitamins, amino acids, proteins, chelating/sequestering agents, hydrotropes, preservatives/antimicrobial agents, bactericides/fungicides, antioxidants, pH control agents, buffering agents, antiperspirant/deodorant agents, heeling agents, colorants and perfumes/fragrances. These ingredients, when used, are added at their usual levels, each generally up to about 10% by weight of the composition and usually totaling up to about 0.001% to about 45% by weight of the composition."

The patent further discloses in Column 39 the following:

"Examples of vitamins useful in the present invention which provide the hair with valuable nutrition include vitamin A (as retinyl acetate, propionate or palmitate) provitamin A (based on carrot extract, as .beta.-carotene), vitamin B.sub.1 (as thiamine mononitrate), vitamin B.sub.2 (as riboflavin), vitamin B.sub.3 (as niacinamide), vitamin B.sub.5 (as pantothenic acid), provitamin B.sub.5 (as panthenol), vitamin B.sub.6 (as pyridoxine hydrochloride, dioctenoate, dilaurate, dipalmitate or tripalmitate), vitamin B.sub.12 (as cyanocobalamin), vitamin. B.sub.15 (as pangamic acid), vitamin C (as ascorbic acid), vitamin D.sub.2 (as ergocalciferol), vitamin D.sub.3 (as cholecalciferol), vitamin E (as dl-.alpha.-tocopherol acetate, linoleate or nicotinate), vitamin F (as glyceryl linoleate and glyceryl linolenate), vitamin K.sub.1 (as phytonadione), vitamin K.sub.3 (as menadione), paba (p-aminobenzoic acid), choline, folic acid, biotin, allantoin biotin, retinol, inositol, allantoin calcium pantothenate, licithin (choline di-C.sub.16-C.sub.18 glycerophosphate), cholesterol, PEG 16 soya sterol, bisabolol, bioflavoniod and mixtures thereof. Preferred vitamins are provitamin A, vitamin B.sub.1, vitamin B.sub.2, provitamin B.sub.5, vitamin B.sub.6, vitamin B.sub.12 and vitamin E. Typical levels of vitamin are from about 0% to about 7% by weight of the composition."

The patent further discloses in Column 40 and 41 the following:

"Examples of preservatives or antimicrobial agents that function as bactericides and/or fungicides useful in the present invention include glutaraldehyde, formaldehyde, paraformaldehyde, glyoxal, benzoic acid, salicylic acid, sorbic acid, dehydroacetic acid, benzyl alcohol, ethanol, 2-phenoxyethanol, chlorohexidine hydrochloride, triclosan, chloroacetamide, p-chloro-m-xylenol, 1-(3-chloroallyl)-3,5,7-triaza-1-azoniaadamantane chloride, methyl paraben, propyl paraben, butyl paraben, benzyl paraben, imidazolidinyl urea, diazolidinyl urea, monomethylol dimethyl hydantoin (MDM hydantoin), dimethylol dimethyl hydantoin (DMDM hydantoin), iodopropylnyl butylcarbamate, 2-bromo-2-nitropropane-1,3-diol, 2-octyl-4-isothiazolin-3-one, 5-chloro-2-methyl-4-isothiazolin-3-one (methylchloroisothiazoline), 2-methyl-4-isothiazolin-3-one (methylisothaizoline), N-(3-chloroallyl) hexaminium chloride and dicocodimethylammonium chloride. Preferred is a combination of methyl isothiazoline and chloromethyl isothiazoline as described in U.S. Pat. No. 4,265,899 sold under the trade name Kathon CG by Rohm and Haas Company which is incorporated herein by reference. Typical levels of preservative used to control bacterial or fungal action are from about 0.001% to about 4% by weight of the composition."

The Eilers Published Patent Application discloses:

"Rounded particles may be used as an abrasive during a microdermabrasion procedure. Rounded particles may be propelled against skin within a treatment area to treat the skin. The rounded particles may abrade portions of the skin within the treatment area. The rounded particles used in a microdermabrasion procedure may be mixed with other abrasives and materials. The rounded particles may be glass beads. The rounded particles may be coated with other materials such as coloring agents, vitamins, lotion, or antibacterial agents."

The patent application essentially discloses a microdermabrasion chemical solution. It includes, for example, in Section 49:

"In certain embodiments, rounded particles 20 may be mixed with other abrasive particles. For example, the rounded particles 20 may be mixed with irregularly shaped, sharp-edged aluminum oxide particles or sand particles (silicon dioxide). The rounded particles 20 may also be mixed with other types of materials. For example, the rounded particles 20 may be mixed with micro-beads of lotion or antibacterial agent. In certain embodiments, a portion of the rounded particles 20 may be coated with a material. For example, a portion of the rounded particles 20 may be coated with a lubricity agent, a lotion and/or an antibacterial agent. A lubricity agent may be added to the rounded particles 20 to reduce the abrasive effect of the particles. Other materials that may be mixed with or coated on the rounded particles 20 may include, but are not limited to coloring agents, vitamins (such as B complex vitamins and vitamin E), bleaching agents, drying agents, and unguents."

The Rhoades Patent discloses:

"A cream moisturizer for resurfacing human skin is provided with a suspension of microcrystals of alumina (Al.sub.2 O.sub.3) in a ratio of approximately 14 grams per ounce of moisturizer cream. The cream moisturizer is buffed into the epidermal layer of the skin with a closed-cell sponge pad driven by a vibrator. The alumina microcrystals buffs an epidermal layer off the skin to provide a soft smooth surface, thereby rejuvenating the skin."

The patent discloses the following elements:

"14 GRAMS OF ALUMINUM OXIDE CRYSTALS (ALUMINA) AL.sub.2 O.sub.3 PER 1 OUNCE OF CREME
VITAMIN A
WATER
WHEAT (TRITICUM VULGARE) GERM
OIL/CAPRIC TRIGLYCERIDE
CATARRHAL ALCOHOL
TOCOPHEROL
BEMZOPHENONE-3
SODIUM CATARRHAL SULFATE
CARROT (DAUCUS CAROTA) EXTRACT
PEANUT (ARACHIS HYPOGAEA) OIL
ISOPROPYL MYRISTATE
PROPYLENE GLYCOL
WHEAT (TRITICUM VULGARE) GERM EXTRACT
WHEAT (TRITICUM VULGARE) BRAN EXTRACT
SORBIC ACID
RETINYL PALMITATE
DEHYDROACETIC ACID
METHYLPARBEN
ASCORBYL PALMITATE
AMINOMETHYL PROPANOL
PROPTLPARABEN
CITRIC ACID
PANTHENOL
LECITHIN"

The patent also discloses in Column 13:

"Alkylmethyl siloxanes with varying degrees of substitution can be used to increase water retained by the skin. Siloxanes such as stearyl dimethicone, known as 2503 Wax, C30-45 alkyl methicone, known as AMS-C30 wax, and stearoxytrimethylsilane (and) stearyl alcohol, known as 580 Wax, each available from Dow Coming®, Midland, Mich., USA. Additional alkyl and phenyl silicones may be employed to enhance moisturizing properties. Resins such as dimethicone (and) trimethylsoiloxysilicate, known as Dow Coming®. 593 or Cyclomethicone (and) Trimethylsiloxysilicate, known as Dow Corning®. 749 fluid, may be utilized to enhance film formation of skin care products. When used, the petrolatum, wax or hydrocarbon or oil component is included in the formulations at a concentration of about 1 to about 20 weight percent, more preferably about 1 to about 12 weight percent. When used, the silicone resins can be included from about 0.1 to about 10.0 weight percent."

The patent further discloses:

"Specific examples of suitable fatty esters for use in the formulation of this invention include isopropyl myristate, isopropyl palmitate, caprylic/capric triglycerides."

Referring to Column 15, the patent discloses:

"The cosmetically acceptable composition of this invention may include one or more antioxidants, which include, but are not limited to ascorbic acid, BHT, BHA, erythorbic acid, bisulfite, thioglycolate, tocopherol, sodium metabisulfite, vitamin E acetate, and ascorbyl palmitate."

Referring to Column 16, the patent discloses:

"The cosmetically acceptable composition of this invention may include one or more preservatives. Example of preservatives, which may be used include, but are not limited to 1,2-dibromo-2,4-dicyano butane (Methyldibromo Glutaronitrile, known as MERGUARD®, ONDEO Nalco Chemical Company, Naperville, Ill., USA), benzyl alcohol, imidazolidinyl urea, 1,3-bis(hydroxymethyl)-5,5-dimethyl-2,3-imidazolidinedione (e.g., DMDM Hydantoin, known as GLYDANT®, Lonza, Fairlawn, N.J., USA.), methylchloroisothiazolinone and methylisothiazolinone (e.g., Kathon®, Rohm & Haas Co., Philadelphia, Pa., USA), methyl paraben, propyl paraben, phenoxyethanol, and sodium benzoate, and mixtures thereof."

Claim 1 of the '618 Brandt Patent reads as follows:

"A process for producing a cosmetically acceptable composition comprising preparing a mixture of an aqueous solution of a copolymer, an aqueous hydroxide solution, a sulfite solution, deionized water and a hydrophobic amine; stirring the mixture thoroughly, placing the mixture into a heating vessel and stirring consistently, pressurizing and venting the heating vessel, heating the heating vessel, cooling the heating vessel to ambient temperature, and collecting an aqueous solution of hydrophobically modified copolymer."

Claim 1 of the European Patent Application reads as follows:

"Cosmetic formulation comprising 99.9 weight-%-70 weight-% of a basic cosmetic formulation selected from the group of transparent pearly lotion, gel cologne with sparkles, pearlescent waterproof sun creme, bronze self tanning cream, sunscreen creme, pearl bronze/copper suntan cream, Icy gel toothpaste, face mask for oily skin, moisturizing body veil, clarifying bright lotion, snow white body cream, cleansing scrub, silky BHA lotion, sunshine body cream, skin moisturizing gel, liquid pearl bath soap, bath dusting powder, bath and shower gel, highlighting hair gel, conditioner, low pH shampoo, sparkle hair spray, festival hair gel, iridescent hair conditioner, conditioning shampoo, pearly foundation cream, blush stick, face bronze pressed powder, silky finish loose face powder, liquid makeup, body veil, earthtone makeup powder, liquid foundation, creamy peral blush, sheer leg makeup, face bronzer with sunscreen, silky face powder, shimmering pearl pressed powder blush, all purpose color stick, dual face powder, radiance pressed powder blush, gel blush frost, sparkling ruby nail enamel, poured eye shadow, cream eye shadow, emulsion cream mascara, eye shadow, liquid eyeliner, pressed powder eye shadow, emulsion cream eye shadow, charcoal silky powder eyeliner, loose powder eye shadow, concealer, sheer satin pressed powder eye shadows, crayon eye shadow, velvety pressed powder eye shadow, waterproof mascara, slender stick eye shadow, silky pressed powder eye shadow, lipstick, fair taupe lipstick, lip gloss with sunscreen, glossy lipstick, shimmering brick lipstick, lip pomade, soft lipstick, pressed lip powder, long wear lipstick, lipstick with sunscreen, lip glaze-formulation and 0.01-30 weight-% glasses or color glass or glass ceramics or ceramics or glass powders or color glass powders or glass ceramic powders or ceramic powders or composite materials comprising glass or glass ceramics or ceramic powders or mixtures of glass, ceramic and glass ceramic powders."

There is a significant need for an improved cosmetic skin exfoliating cream, which eliminates the use of microcrystals which, if not properly administered, can scar gentle facial skin.

SUMMARY OF THE INVENTION

The present invention is a microdermabrasion cream which eliminates the use of microcrystals which can potentially scar skins during a microdermabrasion process and is a cream which consists of the following combination of ingredients which can be safely utilized for microdermabrasion of facial skin. The present invention cream contains the following ingredients: deionized Water, Titanium Dioxide, Carbomer, Glycerin, Disodium EDTA, Caprylic/Capric Triglycerides, Polysorbate 20, *Citrus Limon* (Lemon) Peel Oil, Sodium Hydroxide, Menthol; Cyclomethicone, Dimethicone, *Carica Papaya* (Papaya Fruit), *Ananas Sativus* (Pineapple Fruit), *Cucumis Sativus* (Cucumber) Extract, Glycereth-7, *Bambusa Arundinacea* Stem Powder, Methylchloroisothiazolinone and Methylisothiazolinone. None of these ingredients are the same as alumina.

It is an object of the present invention to provide a microdermabrasion cream which eliminates the use of microcrystals in order to avoid possibly scarring skin during a microdermabrasion process.

Further novel features and other objects of the present invention will become apparent from the following detailed description, discussion and the appended claims, taken in conjunction with the drawings.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

The present invention is a microdermabrasion cream which eliminates the use of microcrystals which can potentially scar skins during a microdermabrasion process and is a cream which consists of the following combination of ingredients which can be safely utilized for microdermabrasion of facial skin. The present invention cream contains the following ingredients: Deionized Water, Titanium Dioxide, Carbomer, Glycerin, Disodium EDTA, Caprylic/Capric Triglycerides, Polysorbate 20, *Citrus Limon* (Lemon) Peel Oil, Sodium Hydroxide, Menthol; Cyclomethicone, Dimethicone, *Carica Papaya* (Papaya Fruit), *Ananas Sativus* (Pineapple Fruit), *Cucumis Sativus* (Cucumber) Extract, Glycereth-7, *Bambusa Arundinacea* Stem Powder, Methylchloroisothiazolinone and Methylisothiazolinone. None of these ingredients are the same as alumina.

The present invention microdermabrasion cream preferably includes the following percentages ranges for its intended use as a cream which consists of the following percentage ranges, which by way of example can be in grams, which combination of ingredients which can be safely utilized for microdermabrasion of facial skin: Deionized Water 25.00-95.00, Titanium Dioxide 0.01-5.00, Carbomer 0.05-1.00, Glycerin 0.50-10.00, Disodium EDTA 0.01-0.50, Caprylic/Capric Triglycerides 0.50-15.00, Polysorbate 20 0.10-5.00, *Citrus Limon* (Lemon) Peel Oil 0.01-2.00, Sodium Hydroxide 0.01-2.5, Menthol 0.001-2.00, Cyclomethicone 0.1-6.00, Dimethicone 0.1-6.00, *Carica. Papaya* (Papaya Fruit) 0.01-5.00, *Ananas Sativus* (Pineapple Fruit) 0.01-5.00, *Cucumis Sativus* (Cucumber) Extract 0.01-2.00, Glycereth 7-0.10-5.00; *Bambusa Arundinacea* Stem Powder 0.01-20.00; Methylchloroisothiazolinone 0.04-0.08 and Methylisothiazolinone 0.04-0.08.

While the percentages have been listed in grams, it will be appreciated that the percentages apply to any weight factor within the ranges as discussed above and therefore, the percentages of each product regardless of the weight measure are as follows: Deionized Water 25.00-95.00, Titanium Dioxide 0.01-5.00, Carbomer 0.05-1.00, Glycerin 0.50-10.00, Disodium EDTA 0.01-0.50, Caprylic/Capric Triglycerides 0.50-15.00, Polysorbate 20 0.10-5.00, *Citrus Limon* (Lemon) Peel Oil 0.01-2.00, Sodium Hydroxide 0.01-2.5, Menthol 0.001-2.00, Cyclomethicone 0.1-6.00, Dimethicone 0.1-6.00, *Carica Papaya* (Papaya Fruit) 0.01-5.00, *Ananas Sativus* (Pineapple Fruit) 0.01-5.00, *Cucumis Sativus* (Cucumber) Extract 0.01-2.00, Glycereth 7-0.10-5.00; *Bambusa Arundinacea* Stem Powder 0.01-20.00; Methylchloroisothiazolinone 0.04-0.08 and Methylisothiazolinone 0.04-0.08.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. A microdermabrasion cream consisting of: Deionized Water, Titanium Dioxide, Carbomer, Glycerin, Disodium EDTA, Caprylic/Capric Triglycerides, Polysorbate 20, *Citrus limon* (Lemon) Peel Oil, Sodium Hydroxide, Menthol, Cyclomethicone, Dimethicone, *Carica papaya* fruit (Papaya Fruit), *Ananas sativus* fruit (Pineapple Fruit), *Cucumis sativus* (Cucumber) Extract, Glycereth-7, *Bambusa arundinacea* Stem Powder, Methylchloroisothiazolinone and Methylisothiazolinone.

2. A microdermabrasion cream consisting of, in grams:
Deionized Water 25.00-95.00, Titanium Dioxide 0.01-5.00, Carbomer 0.05-1.00, Glycerin 0.50-10.00, Disodium EDTA 0.01-0.50, Caprylic/Capric Triglycerides 0.50-15.00, Polysorbate 20 0.10-5.00, *Citrus limon* (Lemon) Peel Oil 0.01-2.00, Sodium Hydroxide 0.01-2.5, Menthol 0.001-2.00, Cyclomethicone 0.1-6.00, Dimethicone 0.1-6.00, *Carica papaya* fruit (Papaya Fruit) 0.01-5.00, *Ananas sativus* fruit (Pineapple Fruit) 0.01-5.00, *Cucumis sativus* (Cucumber) Extract 0.01-2.00, Glycereth-7-0.10-5.00; *Bambusa arundinacea* Stem Powder 0.01-20.00; Methylchloroisothiazolinone 0.04-0.08 and Methylisothiazolinone 0.04-0.08.

3. A microdermabrasion cream consisting of, in percentages:
Deionized Water 25.00-95.00, Titanium Dioxide 0.01-5.00, Carbomer 0.05-1.00, Glycerin 0.50-10.00, Disodium EDTA 0.01-0.50, Caprylic/Capric Triglycerides 0.50-15.00, Polysorbate 20 0.10-5.00, *Citrus limon* (Lemon) Peel Oil 0.01-2.00, Sodium Hydroxide 0.01-2.5, Menthol 0.001-2.00, Cyclomethicone 0.1-6.00, Dimethicone 0.1-6.00, *Carica papaya* fruit (Papaya Fruit) 0.01-5.00, *Ananas sativus* fruit (Pineapple Fruit) 0.01-5.00, *Cucumis sativus* (Cucumber) Extract 0.01-2.00, Glycereth-7-0.10-5.00; *Bambusa arundinacea* Stem Powder 0.01-20.00; Methylchloroisothiazolinone 0.04-0.08 and Methylisothiazolinone 0.04-0.08.

* * * * *